United States Patent [19]
Nishina et al.

[11] Patent Number: 5,582,795
[45] Date of Patent: Dec. 10, 1996

[54] HOLD-TRANSFER SYSTEM FOR EXTRACTION CONTAINERS

[75] Inventors: Takashi Nishina, Kashiwa; Ryoichi Ito, Nishinomiya, both of Japan

[73] Assignees: Furuno Electric Company, Limited, Hyogo; Mitsui Pharmaceuticals, Inc., Tokyo, both of Japan

[21] Appl. No.: 379,491

[22] PCT Filed: Jun. 23, 1994

[86] PCT No.: PCT/JP94/01001

§ 371 Date: Apr. 5, 1995

§ 102(e) Date: Apr. 5, 1995

[87] PCT Pub. No.: WO95/00853

PCT Pub. Date: Jan. 5, 1995

[30] Foreign Application Priority Data

Jun. 25, 1993 [JP] Japan .................................. 5-180664

[51] Int. Cl.$^6$ ............................................. G01N 35/04
[52] U.S. Cl. ............................ 422/65; 422/63; 422/104; 436/43; 436/47; 198/465.2; 198/803.01
[58] Field of Search ........................... 422/63, 65, 67, 422/99, 100, 102, 104; 436/43, 47, 49, 180; 198/465.2, 803.01, 795; 141/130, 168

[56] References Cited

U.S. PATENT DOCUMENTS

| | | | |
|---|---|---|---|
| 3,526,125 | 9/1970 | Gilford et al. ........................ | 422/65 X |
| 3,832,140 | 8/1974 | Lorch et al. .............................. | 422/65 |
| 3,917,455 | 11/1975 | Bak et al. .................................. | 422/64 |
| 4,039,288 | 8/1977 | Moran ....................................... | 422/65 |
| 4,077,444 | 3/1978 | Gilson et al. ........................... | 141/130 |
| 4,517,160 | 5/1985 | Galle et al. ............................... | 422/65 |
| 4,595,562 | 6/1986 | Liston et al. ............................. | 422/65 |
| 4,692,308 | 9/1987 | Riley et al. .............................. | 422/65 |
| 4,890,930 | 1/1990 | Nohso ..................................... | 366/208 |
| 5,397,542 | 3/1995 | Nelms et al. ............................ | 422/104 |

FOREIGN PATENT DOCUMENTS 59-22905  5/1984  Japan .

*Primary Examiner*—Long V. Le
*Attorney, Agent, or Firm*—Jordan and Hamburg

[57] ABSTRACT

A hold-transfer system for extraction containers has a main body and a cassette detachable from the main body. The cassette has holding devices for holding extraction containers in an upright position, an endless traveling member carrying the holding devices arranged in a row, and a driving rotor and a driven rotor engaging the endless traveling member about perimeters thereof. The endless traveling member has rotatable support member for rotatably supporting the holding devices with lower portions of the holding devices protruding below the rotatable support members and accessible from beneath the cassette. The main body has a driving motor for driving the driving rotor and an identifying device, installed at a reading position relative to a specified position for an extraction, for identifying an identification mark associated with one of the extraction containers. The identifying device includes a reading device for reading the identification mark and a rotating mechanism for engaging and rotating the lower portion of the holding device to rotate the extraction container to expose the identification mark to the reading device.

12 Claims, 4 Drawing Sheets

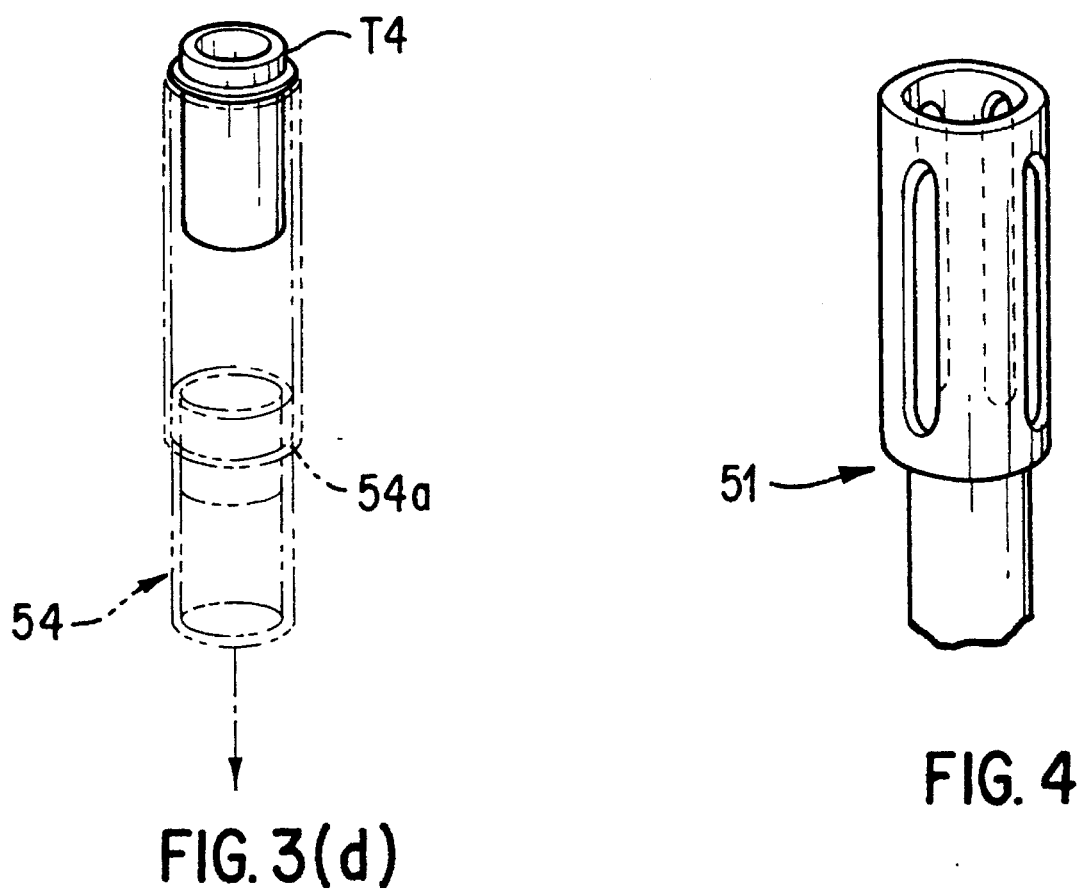

HOLD-TRANSFER SYSTEM FOR EXTRACTION CONTAINERS

BACKGROUND OF THE INVENTION

This invention relates to a hold-transfer system for extraction containers which are used for analyzing liquids such as blood and medicines in the medical field.

There are known types of hold-transfer systems for extraction containers such as a radial type, a linear type and a bellows type. The radial type comprises a replaceable drum to hold extraction containers such as test tubes along its circumferential line, whereby the liquid in the extraction container is extracted with a pipette nozzle as the drum rotated. The linear type comprises a plural rectangular cases to hold extraction containers upright in a straight line, whereby the liquid in the extraction container is extracted with a pipette nozzle while a plural of cases are transferred to the x-y direction in order. The bellows type comprises cartridges to be inserted container, a bellows to hold the cartridges in a line specified distance apart and a rotary shaft around which the bellows is wound, whereby the liquid in container is extracted with a pipette nozzle while one end of the bellows is pulled out in order. And also, there is another known type of a hold-transfer system disclosed in Japanese Patent Publication of No. 58-501145, which is a linking type. The linking type comprises a charging unit to charge a plurality of containers, a storage unit and a rotatably drum-shaped transfer unit installed between the charging unit and the storage unit, wherein the liquid in container is extracted at the transfer unit.

These above described types have some problems respectively. According to the drum type, a drum holding extraction containers is so replaceable that time for replacement of container is short. But the installation square area increases as the drum size increases, therefor, its capacity is limited to about 30 containers at maximum. According to the linear type, continuous extraction from a large number of containers is possible when the number of cases is increased. But a long time is required for replacing containers because containers are replaced by replacement of rectangular cases. According to the bellows type, capable extraction times to each containers can be only once. According to the linking type, extraction of a large number of containers is automatically done. But the linking type has a complexity of its construction. And further, these above types such as the drum type, the linear type, the bellows type and the linking type have a limitation of container types.

The present invention is embodied in view of problems which the prior arts possess, hence it is a primary object thereof to present a hold-transfer system for extraction containers, which is capable of holding a large number of containers in a small space, enables replacement of containers to facilitate as a whole, as well as is capable of operations such as extraction, an identification and transfer in series and repeatedly, and enables the above identification to be achieve reliably. It is another object to present a hold-transfer system, for extraction containers, which is capable of holding and transfering various shaped containers.

A hold-transfer system for extraction of containers according to the present invention, in order to solve the above problems, comprises a main body and cassettes detachable from the main body. The cassette comprises holding means for holding extraction containers in an upright position, an endless travelling unit with a large number of said holding means in a row, a driving rotor and a driven rotor on which the endless travelling unit is laid across with tension so that the endless travelling unit can travel. The main body comprises driving means for the driving rotor and an identifying means for a indentifying mark on the container. The identifying means is installed at a position relative to a specified position for extraction. Accordingly, operations such as extraction, identification, and transfer will be done in series and repeatedly as the endless travelling unit travels.

Another embodiment of the hold-transfer system for extraction containers according to the present invention comprises holding means for holding extraction containers having identification marks in an upright position, an endless travelling unit with a large number of the holding means in a row, a driving rotor and a driven rotor on which the endless travelling unit is laid across with tension so that the endless travelling unit can travel, a intermittent driving means for the driving rotor, a rotating means for rotating the extraction container while the endless travelling unit is stopped, an extraction means for extracting liquid from the container, and an identifying means for identifying a mark on the container. The identifying means is installed at a position relative to a specified position for extraction. Accordingly, operations such as extraction, identification, and transfer are intermittently carried out for the containers as the endless travelling unit travels.

In addition, some containers comprise adapters which are inserted into the holding means and container propers which are inserted into the adapters. This invention has a plurality of types of adapters applicable to various shaped container propers.

The present invention of hold-transfer system for extraction containers described above is set on a long table. Because the endless travelling unit is laid across with tension between the driving rotor and the driven rotor, when the shaft-to-shaft distance between the driving and driven rotors increases, the system will extend forming an oblong configuration. Further, when a large number of holding means are arranged in a row on this extended long endless travelling unit, the number of extraction containers becomes large. In addition, the construction of the cassette detachable from the main body enables one to replace a large number of extraction containers in a short time. And further, the intermittent travelling of the endless travelling unit enables extraction and identification to be done while the endless travelling unit stops.

Additionally, according to the invention, the various shaped containers are held by the same holding means because a container proper, such as a test tube, is inserted into the holding means via the adaptor and, the invention includes a plurality of types of adapters applicable to the various shaped container propers.

BRIEF DESCRIPTION OF DRAWINGS

FIG. 4 shows slits of an adaptor.

DETAILED DESCRIPTION OF THE INVENTION

Figure 1:
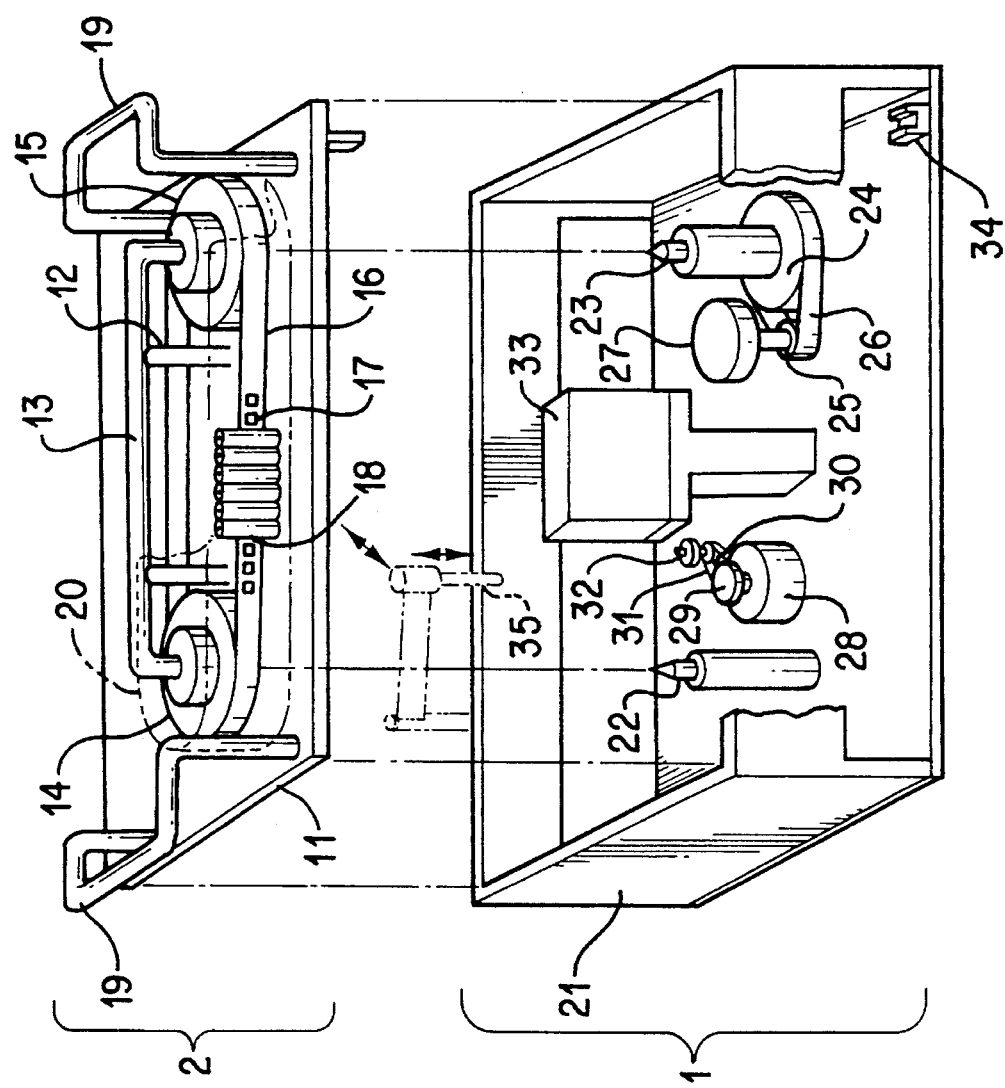
FIG. 1 shows a construction of a hold-transfer system according to this invention.

The invention will be described in further detail with reference to the accompanying drawings. FIG. 1 is a structural drawing of a hold-transfer system for extraction containers according to the invention. In FIG. 1, numeral 1 and numeral 2 indicates a main body and a cassette respectively that compose the hold-transfer system.

In the cassette 2, a longitudinal frame 12 is erected on a bottom plate 11. A transverse frame 13 is laid across the longitudinal frame 12. A driven sprocket (driven rotor) 14 and a driving sprocket (driving rotor) 15 are mounted at respective ends of the transverse frame 13. The sprockets 14, 15 are rotatably supported in the horizontal plane. Chains (endless travelling unit) 16 are stretched between the sprockets 14, 15. Metal fittings 17 are arranged on the chain 16 at specified intervals. A tube case (holding means) 18 is rotatably supported at the metal fitting 17. A test tube (not illustrated) is inserted into the tube case (holding means). Transparent guards 20 are installed along inner and outer circumferential lines of a passage on which the rotatable tube case 18 travels(in the illustrated example, the outer circumference only is illustrated).

In addition, handles 19, 19 are installed on both sides of the bottom plate 11 for lifting the whole cassette 2 with both hands. When lifting cassette 2 with both hands, there is a limitation to the total length of the cassette 2. Its preferable length is about 400 mm. With this length, a total of 42 pieces of tube cases are arranged in a row. There are two or more sets of cassettes for one main body 1. While one cassette 2 is installed on the main body 1, test tubes in another cassette 2 are replaced.

The main body 1 has a housing 21 with an open top. A driven shaft 22 and a driving shaft 23 are rotatably installed in an upright position to the housing 21, respectively. The driving shaft 23 is rotated and driven by a first motor 27 via timing pulleys 24, 25 and timing belt 26. A second motor 28 is installed in the housing 21. A rubber pulley 32 is installed in an upright position to rotate in the horizontal plane. The rubber pulley 32 is rotated and driven by the second motor 28 via a timing pulleys 29, 30 and timing belt 31. In addition, bar code reader 33 is installed in an upright position at the vicinity of the center of the housing 21.

The bottom plate 11 of the above-mentioned cassette 2 fits in the housing 21 of the main body 1. In this occasion, the driven shaft 22 latches the driven sprocket 14, and the driving shaft 23 latches the driving sprocket 15. This embodiment will be described in detail later. The rubber pulley 32 contacts with the tube case 18. The bar code reader 33 is located at the position where it can read the bar code on a test tube inserted in the tube case 18, which is not illustrated. When the photo sensor 34 detects the installation of the cassette 2 in the main body 1, the motors 27, 28 are ready for operation. Numeral 35 is a pipette nozzle for extracting liquid form the test tube. The pipette nozzle 35 is installed to the position where it can extract the liquid from the test tube after its bar code is read by the bar code reader 33. The pipette nozzle 35 is supported so as to elevate and revolve.

Figure 2:
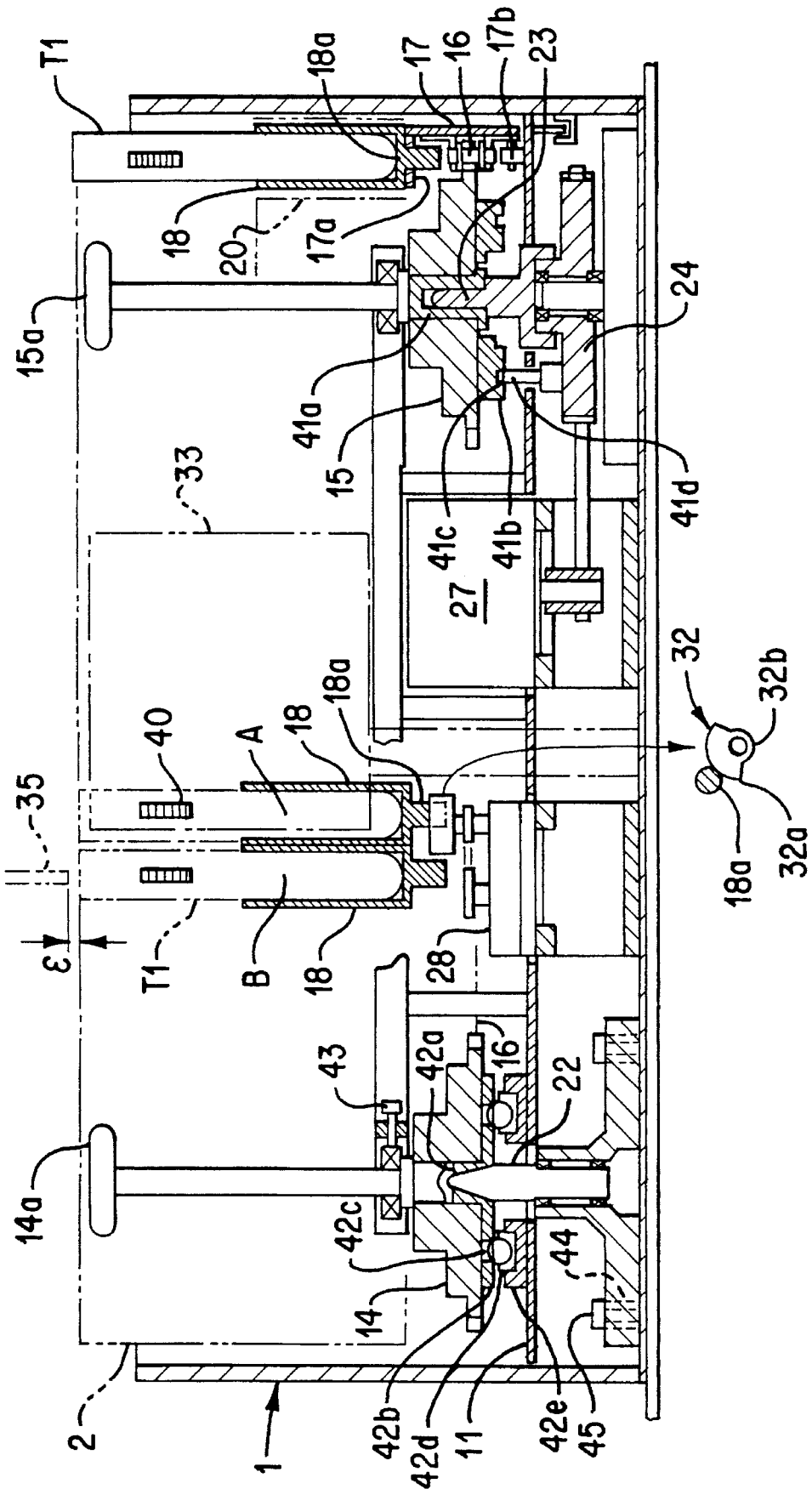
FIG. 2 shows a cross-sectional view of the hold-transfer system.

FIG. 2 shows a cross-sectional view of the main body 1 in which the cassette section 2 is installed. As shown in detail with FIG. 2, the metal fittings 17 are shaped like an inverse L-letter respectively and are mounted to the chain 16 by a link of the chain 16. A shaft 18a of the tube case 18 is supported rotatably via a bearing 17a of the metal fitting 17. A roller 17b on the bottom plate 11 is mounted below the metal fitting 17 so as to support the weight above the tube case 18. Transparent guards 20 are installed for protection of the tube case 18 along the inner and outer circumferential lines of the travelling passage of the tube case 18. A test tube T1 with a bar code (identification mark) 40 is inserted into the tube case 18. The bar code (identification mark) 40 is read by the bar code reader 33 at a position A shown in FIG. 2.

A laser or LED type automatic scanning system is used for this bar code reader 33. At the position A, the rubber pulley 32 contacts with the shaft 18a of the tube case 18. The rubber pulley 32 is continuously rotated with the motor 28. The rubber pulley 32 has a major diameter section 32a and a minor diameter section 32b. The shaft 18a rotates while contacting the major diameter section 32b. The shaft 18a does not rotate while separated from the minor diameter section 32b. The motor 27 rotates while this shaft 18a does not rotate. The motor 27 stops after the chain 16 travels by one pitch. This pitch is the distance between the tube cases 18 arranged in a row. In this way, the chain 16 intermittently travels. When the bar code 40 is read, the test tube T1 is identified and travels to a position B. At the position B, the pipette nozzle 35 is inserted into the test tube T1 and extracts a specified volume of the liquid.

A straight sleeve 41a is fitted to the center of the driving sprocket 15. A dividing plate 41b is mounted to the underneath of the driving sprocket 15. The dividing holes 41c are machined to the dividing plate 41b. The number of dividing holes 41c corresponds to the number of or divisor of the tube cases 18. A positioning pin 41d is installed to the timing pulley 24 so as to fit to the dividing hole 41c. The spindle, which is the tip end of the driving shaft 23, fits into the sleeve 41a and the positioning pin 41d fits into the dividing hole 41, preventing the tube case 18 installed on the chain 16 from deviating from the position relative to the bar code reader 33 or pipette nozzle 35. A taper sleave 42a is fitted to the center of the driven sprocket 14. A dividing plate 42b is mounted to the underneath of the driven sprocket 14. The dividing holes 42c are also machined to the dividing plate 42b. The number of the dividing holes 42c corresponds to the number of or divisor of the tube cases 18. A plunger base 42e is installed to the bottom plate 11. Ball plungers 42d are installed to this plunger base 42e. The number of the ball plungers is about from 2 to 4. The ball plunger 42d is movable vertically and capable of fitting into the dividing hole 42c. So, when the driven sprocket 14 travels by one pitch, the ball plunger 42d goes out one dividing hole 42c and then fits into the next dividing hole 42c. In this way, positioning is achieved for one-pitch travel while the conical portion of the tip end or the driven shaft 22 is fitted into the taper sleeve 42a. The number of the ball plungers 42d is properly determined in view of the torque of the driving motor. It is also possible to move the driven sprocket 14 to the left side of the drawing by a bolt 43. It is also possible to move and fix the driven shaft 22 to the left side of the drawing using an elongated hole 44 and a bolt 44. This enables a tension of the chain 16 to be adjusted. In addition, a steel belt or timing belt may be used as an endless travelling unit in place of the chain 16.

Next, with reference to FIG. 2 an operation of the hold-transfer system according to the invention comprising one main body 1 and two or more cassettes 2 detachable from the main body is described. First, the cassette 2, detached from the main body 1, is placed on a table and test tubes T1 containing a specified liquid are inserted into tube cases 18 in order. In this event, the chain 16 is allowed to travel by rotating either knob 14a or 15b. The knob 14a and 15b are installed in an upright position to the driven sprocket 14 and driving sprocket 15 respectively. Consequently, each test tube T1 can be inserted at the same position. Then, the cassette 2 with test tubes is fitted into the main body 1 and brought to a illustrated condition. The main body 1 and the pipette nozzle 35 have a specific spatial relationship with each other so that the liquid can be extracted from the test tube T1 at the position B.

Then, pressing a start switch of the main body 1 causes the chain 16 to begin intermittent travelling. The intermittent travelling means a travelling mode wherein the chain repeats stopping and travelling by each link with rotating of the rubber pulley 32. The rubber pulley 32 rotates the tube case 18 at the position A while the chain 16 stops. This rotation takes 0.5 seconds per operation. As illustrated, the bar code 40 is only affixed on a part of the outer circumferential face of the test tube T1. However, the tube case 18 rotates at the position A. Consequently, the bar code reader 33 can read the bar code 40 without fail while the tube case 18 makes one rotation at the position A. The automatic scanning type of a bar code reader 33 scans 30–80 times per second. While the tube case 18 makes one rotation for about 0.5 seconds. Consequently, it is enough speed for the bar code reader to read the bar code. This rotating structure of the tube case 18 enables of the insertion of the test tube T1 into the tube case 18 without worrying about the direction of the bar code 40.

The test tube T1 travels to the position B and stops after its bar code 40 is read at the position A. During stopping of the test tube T1, the pipette nozzle 35 lowers into the test tube T1 and extracts the liquid. The test tube T1 has already been identified at the position B because its bar code 40 was read at the position A. Moving of the pipette nozzle 35 such as advance, lowering, and their reverse are synchronized with the intermittent travel of the chain 16. If one test tube T1 is extracted several times, the intermittent travel should be repeated until the content of the test tube T1 is consumed. In this way, continual extraction is achieved. The intermittent travel also enables the test tube T1 to be replace while the chain stops.

When the extractions are completed for a whole cassette 2 in this way, the extracted old cassette 2 is detached from the main body 1 and the standby new cassette 2 is fitted into the main body 1. The extracted test tubes T1 of the old cassette 2 are replaced during extractions from test tubes T1 of the new cassette 2. In this event, replacement is achieved with rotating the knob 14a or 15a. This way saves the time required for inserting new test tubes to the cassette 2.

A specified interval ϵ between the pipette nozzle 35 and the test tube T1 is kept in FIG. 2 when the test tube T1 is directly inserted into the tube case 18. However, there are various shaped test tubes. Therefor, the present invention of the hold-transfer system has adapters 51–54 for the tube case 50 as illustrated in FIG. 3. When these adapters 51–54 used, the same hold-transfer system is applied to a large number of various shaped containers T1–T4.

Figures 3A, 3B, 3C:
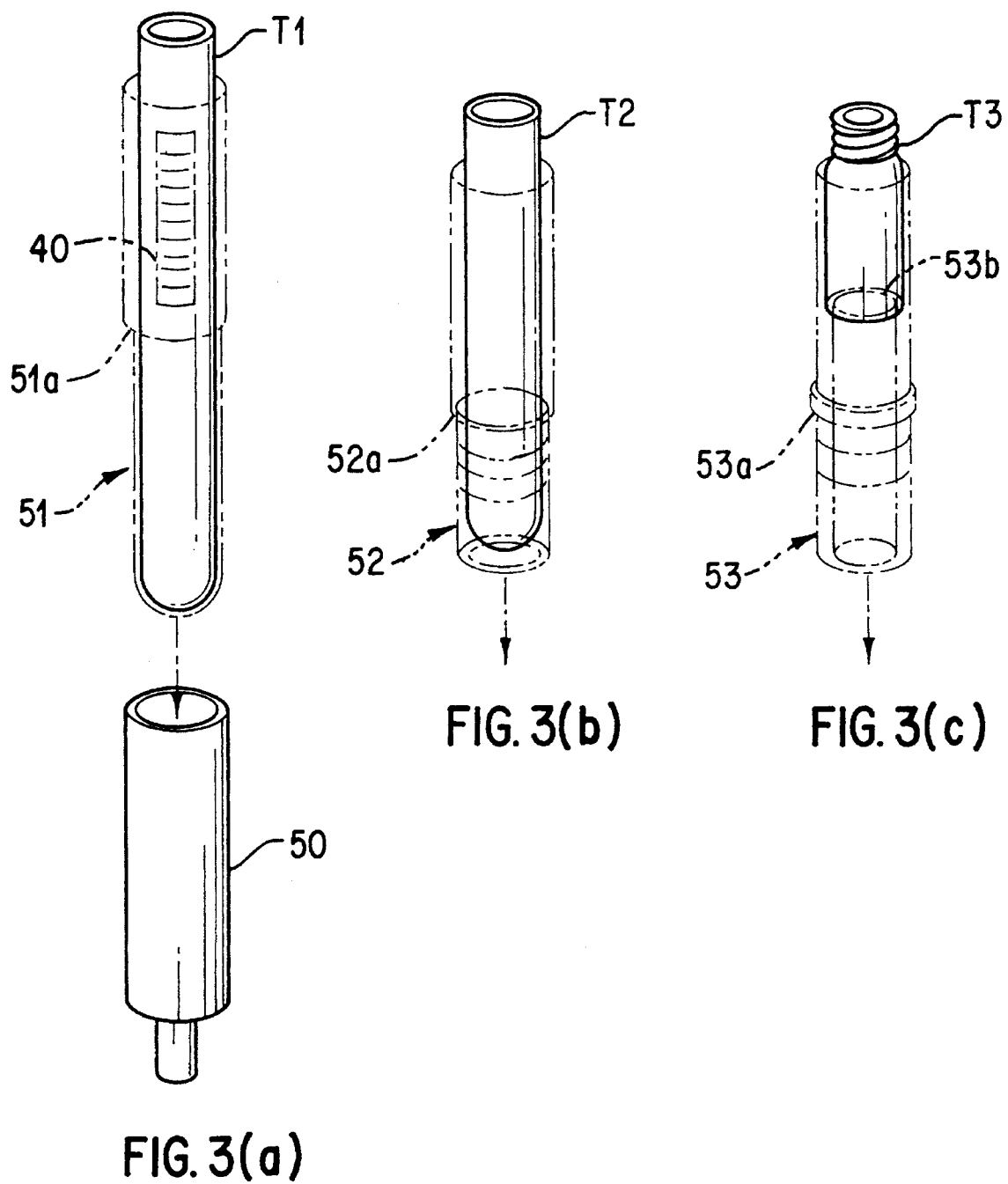
FIG. 3 shows various combinations of extraction containers.

FIG. 3(a) shows an adaptor 51 which is applied to a long test tube T1. The test tube T1 stops at the bottom of the adaptor 51. The stepped portion 51a of the adaptor 51 stops at the top end of the tube case 50. In this way, the interval between the top end of the test tube T1 and the tip end of the pipette nozzle is maintained at a specified value.

FIG. 3(b) shows an adaptor 52 which is applied to a short test tube T2. The lower part from the stepped portion 52a of the adaptor 52 is designed to be short. FIG. 3(c) shows an adaptor 53 for a bottle T3. The adaptor 53 has an inner stepped portion 53b in addition to the stepped portion 53a. The stepped portion 53a stops at the top end of the tube case 50. The bottom of the bottle T3 stops lowering at the inner stepped portion 53b. FIG. 3(d) shows an adaptor 54 for a cup T4. The adaptor 54 has a stepped portion 54a which stops at the top end of the tube case 50. And the cup T4 stops lowering at the entry of the adaptor 54.

In this way, the same hold-transfer system for extraction containers is applied to various shaped containers only by exchanging adapters 51–54 for common tube cases 50. If adapters 52–54 have a 3-bit black line respectively, the types of adapters 52–54, are identified by a reflector type of a fiber sensor.

These above-mentioned adapters 51–54 are made of transparent acryl or provided with longitudinal slits at four places as shown in FIG. 4. Consequently, the bar code 40 can be read without any trouble. In addition, when the bar code on the container happens to break, it is useful that the same bar code as that on the container is affixed on the adaptor. The bar code on the adapters 52–54 can take the place of that on the container.

As described above, this invention of the hold-transfer system for extraction containers has a construction wherein an endless travelling unit is stretched across with tension between a driving rotor and a driven rotor and holding means for holding containers are arranged in a row on this endless travelling unit. Consequently, extending the distance between the driving rotor and the driven rotor allows the hold-transfer system to be equipped with a large number of containers. And also, this invention of the hold-transfer system has a construction for comprising a main body and cassettes detachable from the main body. Consequently, the hold-transfer system enables replacement of a large number of containers at once. If there are two or more cassettes for one main body, it is possible to replace containers in one cassette while extraction from containers in another cassette. The containers are carried intermittently so as to be extracted and identified while stopping. Consequently, operations such as a extraction, a identification and a transfer of the hold-transfer system is enabled in series and repeatedly. In addition, a reliable identification takes place even when marks such as a bar code, etc. is affixed only on a part of the outer circumferential face of the container because the container rotates at the reading mark position.

And further, when there are a plurality of adapters which are applicable to various shaped containers, the various shaped containers are held by the same holding means. Consequently, the same hold-transfer system is used for various shaped types of test tubes. If identification marks are affixed on these adapters, they are useful in place of ones on test tubes at a emergency time.

As described above, the present invention of the hold-transfer system for extraction containers is suitable as one which can hold a large number of containers in a small space, can facilitate replacement of containers as a whole, carries out an extraction, an identification and a transfer in series and repeatedly, and in addition, carries out the above identification reliably. This system is easily applicable to a plurality of various shaped containers.

We claim:

1. A hold-transfer system for extraction containers comprising:

a main body and a cassette detachable from said main body;

said cassette having holding means for holding extraction containers in an upright position, an endless traveling member carrying said holding means arranged in a row, a driving rotor and a driven rotor engaging said endless traveling member about perimeters thereof;

said endless traveling member having rotatable support means for rotatably supporting said holding means with a lower portion of said holding means protruding below said rotatable support means and accessible from beneath said cassette;

said main body having driving means for driving said driving rotor and an identifying means, installed at a reading position relative to a specified position for an extraction, for identifying an identification mark associated with one of said extraction containers; and said identifying means including a reading means for reading said identification mark and a rotating means for engaging and rotating said lower portion of said holding means to rotate said extraction container to expose said identification mark to said reading means.

2. A hold-transfer system according to claim 1 wherein said container includes an adaptor insertable into said holding means and a container proper inserted into said adaptor.

3. A hold-transfer system for extraction containers according to claim 2, wherein there are a plurality of configurations of said adapters applicable to variously shaped container propers.

4. A hold-transfer system for extraction containers according to claim 2, wherein said identification marks are affixed on said adapter.

5. A hold-transfer system for extraction containers according to claim 1 or 2, further comprising at least another cassette identical to said first cassette for said main body.

6. A hold-transfer system for extraction containers according to claim 1 or 2, wherein said driving means drives intermittently so as to transfer and stop repeatedly for each one of said extraction containers held by said endless traveling member.

7. A hold-transfer system for extraction containers according to claim 6, wherein said identifying means operates while said intermittent driving means stops.

8. A hold-transfer system for extraction containers comprising:

a main body and two or more cassettes detachable from said main body;

each of said two or more cassettes having holding means for holding extraction containers in an upright position, an endless traveling member carrying said holding means arranged in a row, a driving rotor and a driven rotor engaging said traveling member about perimeters thereof;

said endless traveling member having rotatable support means for rotatably supporting said holding means with a lower portion of said holding means protruding below said rotatable support means and accessible from beneath said cassette;

said main body having driving means for driving said driving rotor and an identifying means, installed at a reading position relative to a specified position for an extraction, for identifying an identification mark associate with one of said containers;

said identifying means including a reading means for reading said identification mark and a rotating means for engaging and rotating said lower portion of said holding means to rotate said extraction container to expose said identification mark to said reading means; and said containers including variously shaped container propers and a plurality of types of adapters which are applicable to said variously shaped container propers and insertable into said holding means.

9. A hold-transfer system for extraction containers comprising:

holding means for holding extraction containers in an upright position, an endless traveling member carrying said holding means arranged in a row, a driving rotor and a driven rotor engaging said endless traveling member about perimeters thereof;

said endless traveling member having rotatable support means for rotatably supporting said holding means with a lower portion of said holding means protruding below said rotatable support means;

driving means for driving said driving rotor and an identifying means, installed at a reading position relative to a specified position for an extraction, for identifying an identification mark associated with one of said extraction containers: and said identifying means including a reading means for reading said identification mark and a rotating means for engaging and rotating said lower portion of said holding means to rotate said extraction container to expose said identification mark to said reading means.

10. The hold-transfer system for extraction containers according claim 1 wherein one of said driving and driven rotors includes a detent means for providing a bias to retain said holding means at positions aligned with said reading position and said specified position, said positions being space apart by a one pitch distance equal to a center to center distance of said holding means.

11. The hold-transfer system for extraction containers according claim 10 wherein said detent means includes a ball plunger assembly and a dividing hole member functionally coupled to said one of said driving and said driven rotors and said cassette.

12. The hold-transfer system for extraction containers according to any one claims 1, 8 or 9 further comprising a base plate rotatable supporting said driving rotor and said driven rotor and said rotatable support means have a leg member with a roller engaging said base plate to support said rotatable support means.

* * * * *